(12) United States Patent
Westheim

(10) Patent No.: US 8,372,856 B2
(45) Date of Patent: Feb. 12, 2013

(54) HYDRATES OF ERLOTINIB HYDROCHLORIDE

(75) Inventor: Raymond J. H. Westheim, Oss (NL)

(73) Assignee: Synthon BV, Nijmegen (NL)

( * ) Notice: Subject to any disclaimer, the term of this patent is extended or adjusted under 35 U.S.C. 154(b) by 1509 days.

(21) Appl. No.: 11/923,957

(22) Filed: Oct. 25, 2007

(65) Prior Publication Data

US 2008/0167327 A1    Jul. 10, 2008

Related U.S. Application Data

(60) Provisional application No. 60/863,158, filed on Oct. 27, 2006.

(51) Int. Cl.
*A01N 43/54* (2006.01)
*A61K 31/517* (2006.01)

(52) U.S. Cl. ............... 514/266.4; 514/266.3; 544/293

(58) Field of Classification Search ............ 514/266.3, 514/266.4; 544/293
See application file for complete search history.

(56) References Cited

U.S. PATENT DOCUMENTS 5,747,498 A * 5/1998 Schnur et al. .......... 514/266.4

FOREIGN PATENT DOCUMENTS

| EP | 1044969 | 10/2000 |
|---|---|---|
| WO | WO 96/30347 | 10/1996 |
| WO | WO 01/34574 | 5/2001 |
| WO | WO 2004/072049 | 8/2004 |

OTHER PUBLICATIONS

Grunwald, V. et. al., Review, J. Nat. Can. Inst., vol. 95, No. 12, Jun. 18, 2003, pp.*
Pinedo et al.*
McMahon et al.*

\* cited by examiner

*Primary Examiner* — Paul V. Ward
(74) *Attorney, Agent, or Firm* — Mark R. Buscher

(57) ABSTRACT

Erlotinib hydrochloride hydrate is formed from an aqueous solution and is useful as a pharmaceutical and as a purification intermediate.

17 Claims, 6 Drawing Sheets

HYDRATES OF ERLOTINIB HYDROCHLORIDE

The present application claims the benefit of priority under 35 U.S.C. §119(e) from U.S. Provisional Application Ser. No. 60/863,158, filed Oct. 27, 2006, the entire contents of which are incorporated herein by reference.

BACKGROUND OF THE INVENTION

The present invention relates to novel hydrates of erlotinib hydrochloride, a process for preparing them, pharmaceutical compositions thereof and their use as a medicament.

Erlotinib, chemically [6,7-bis(2-methoxyethoxy)-quinazolin-4-yl]-(3-ethynylphenyl)amine of formula 1

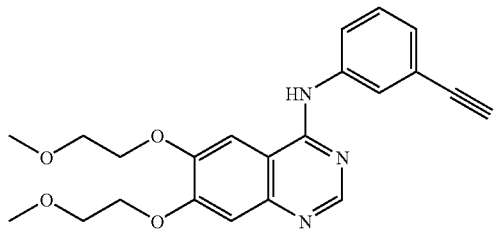

1 is a compound that inhibits the human epidermal growth factor receptor tyrosine kinase, also known as EGFR-TK, that is critical for growth of malignant cells. EGFR over expression is associated with disease progression, and reduced survival. Erlotinib acts by blocking tyrosine kinase activity of EGFR-TK, resulting in inhibition of signaling pathway, and decreased growth of malignant tumors. Erlotinib is thus useful for the treatment of proliferative disorders such as cancers in humans. Erlotinib is marketed as its hydrochloride salt.

WO 96/30347 (U.S. Pat. No. 5,747,498) discloses the preparation of erlotinib hydrochloride in example 20, by reaction of the base in chloroform/ether mixture with 1N HCl. It is only mentioned that it has a melting point of 228-230° C.

European patent application EP 1044969 discloses processes for the synthesis of erlotinib hydrochloride (examples 4, 7 and 9-11). In these processes, alcoholic solvents propan-2-ol, butan-1-ol, butan-2-ol and 2-methoxyethanol were used for the precipitation of the erlotinib hydrochloride by concentrated HCl. No data concerning the crystalline form of the hydrochloride compounds are disclosed except a melting point in example 4 of 226-229° C.

WO 01/34574 disclosed the existence of two polymorphic Forms of erlotinib hydrochloride which were designated as Form A and B. Form B is thermodynamically more stable than Form A. It may be prepared substantially free from polymorph A by crystallization of erlotinib hydrochloride Form A or of the mixture of polymorphs A and B from 2B-ethanol/water mixture. It is also mentioned in the application that example 20 of WO 96/30347 yields a mixture of Form A and B.

More recently WO 2004/072049 disclosed the existence of another polymorph of erlotinib hydrochloride, designated as Form E, which showed similar stability as Form B but with a higher solubility. It may be prepared by precipitation of erlotinib hydrochloride from trifluorotoluene.

The polymorphs disclosed above are anhydrous compounds, i.e. they do not comprise water in the crystalline lattice.

SUMMARY OF THE INVENTION

The present invention relates to the discovery of hydrates of erlotinib hydrochloride. Such compounds can be used as an alternative for the anhydrous erlotinib hydrochlorides in the treatment of proliferative disorders. Further the compounds of the invention have the advantage that they can be prepared by crystallization from an aqueous solution without use of an organic solvent, providing possible purification and ecological benefits.

Accordingly one aspect of the present invention relates to crystalline erlotinib hydrochloride hydrates. Typically the hydrate is a hemihydrate such as hemihydrate Form I, which can be characterized by, inter alia, an XRPD pattern having the following XRPD peaks at 2θ: 5.8, 9.4, 10.0, 11.1, 11.6, 17.5, 18.6, 24.9, and 26.8+/−0.2 degrees or hemihydrate Form II which can be characterized by, inter alia, an XRPD pattern having the following XRPD peaks at 2θ: 5.8, 10.6, 12.1, 14.6, 15.1, 17.3, 19.3, 24.3, 26.3, +/−0.2 degrees.

A second aspect of the present invention relates to a process for the preparation of a hydrate of erlotinib hydrochloride comprising crystallizing erlotinib hydrochloride hydrate from an aqueous solution of erlotinib hydrochloride, preferably in the absence of organic solvent, and typically at a temperature of 20° C. of less. Generally, the process is used to make a hemihydrate such as Form I or Form II.

A third aspect of the invention relates to a pharmaceutical composition comprising a crystalline erlotinib hydrochloride hydrate and a pharmaceutically acceptable excipient. Generally the hydrate is a hemihydrate, such as Form I or Form II. In some embodiments the crystalline erlotinib hydrochloride hydrate is contained in a pharmaceutically effective amount and is frequently in a solid dosage form such as a tablet or capsule.

A fourth aspect of the invention relates to the use of an erlotinib hydrochloride hydrate and their pharmaceutical compositions as a medicament. Preferably the use is for the treatment of cancer wherein the cancer is from the group of brain, squamous cell, bladder, gastric, pancreatic, hepatic, glioblastoma multiform, head, neck, esophageal, prostate, colorectal, lung, renal, kidney, ovarian, gynecological, thyroid, non-small cell lung (NSCLC), refractory, ovarian, or head and neck cancer.

A fifth aspect relates to the use of the erlotinib hydrochloride hydrates for making anhydrous erlotinib hydrochloride.

The XRPD spectra were recorded according to the following settings:

| | |
|---|---|
| Start angle (2θ): | 2.0° |
| End angle (2θ): | 35.0-50° |
| Scan step width: | 0.02° |

-continued

| | |
|---|---|
| Scan step time: | between 1-6 seconds |
| Radiation type: | Cu |
| Radiation wavelengths: | 1.54060 Å (K$\alpha_1$), primary monochromator used |
| Exit slit: | 6.0 mm |
| Focus slit: | 2 mm |
| Divergence slit: | Variable (V20) |
| Antiscatter slit: | 3.37 or 6.17 mm |
| Receiving slit: | 5.25 or 10.39 mm |

The DSC experiments were performed according to the temperature schedule given below:

| | |
|---|---|
| Start temperature: | 25° C. |
| End temperature: | 260° C. |
| Heating rate: | 10° C./min |

The FT-IR experiments were performed according to the KBr-method. The FT-IR spectra were recorded from 600 cm$^{-1}$ to 4000 cm$^{-1}$. From each FT-IR spectrum a blank FT-IR spectrum of KBr was subtracted. That blank IR spectrum was recorded prior to the measurements of the samples.

DETAILED DESCRIPTION OF THE INVENTION

The present invention is based on the discovery of erlotinib hydrochloride hydrates.

A hydrate is a compound that contains water bound thereto. Hydrates are normally qualified by their degree of hydration, i.e. the molar amount of water bound to a molecule. A monohydrate typically has a degree of hydration of 0.9 to 1.05 molar equivalents of water per mol of erlotinib. A hemihydrate typically has a degree of hydration between 0.45 and 0.55 molar equivalents of water. While the hydrate compounds of the present invention are not limited to any particular degree of hydration, the hemihydrate compound is generally preferred.

Figure 1:
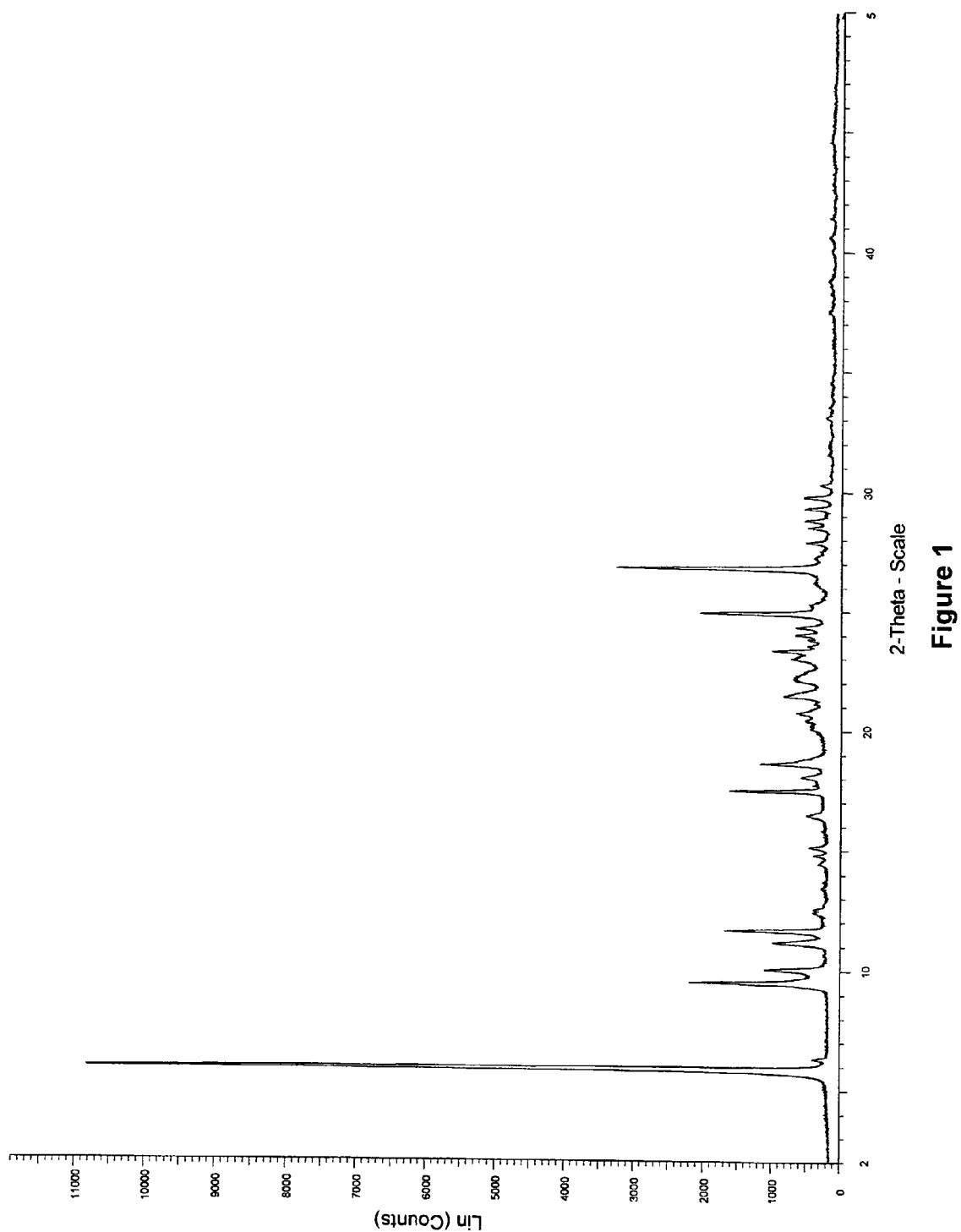
FIG. 1. XRPD spectra of erlotinib hydrochloride hemihydrate Form I.
Figure 3:
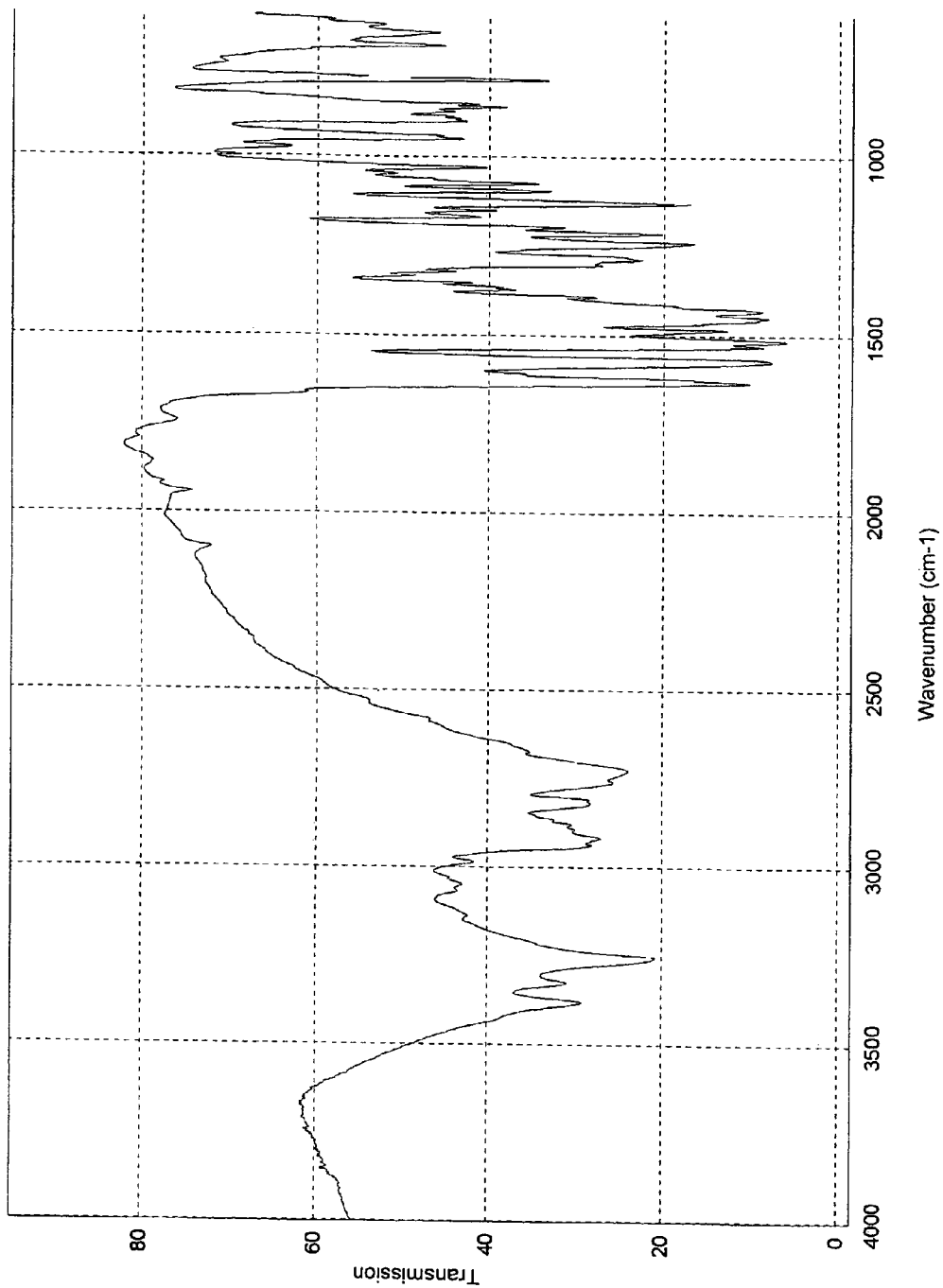
FIG. 3. FT-IR spectra of erlotinib hydrochloride hemihydrate Form I.
Figure 4:
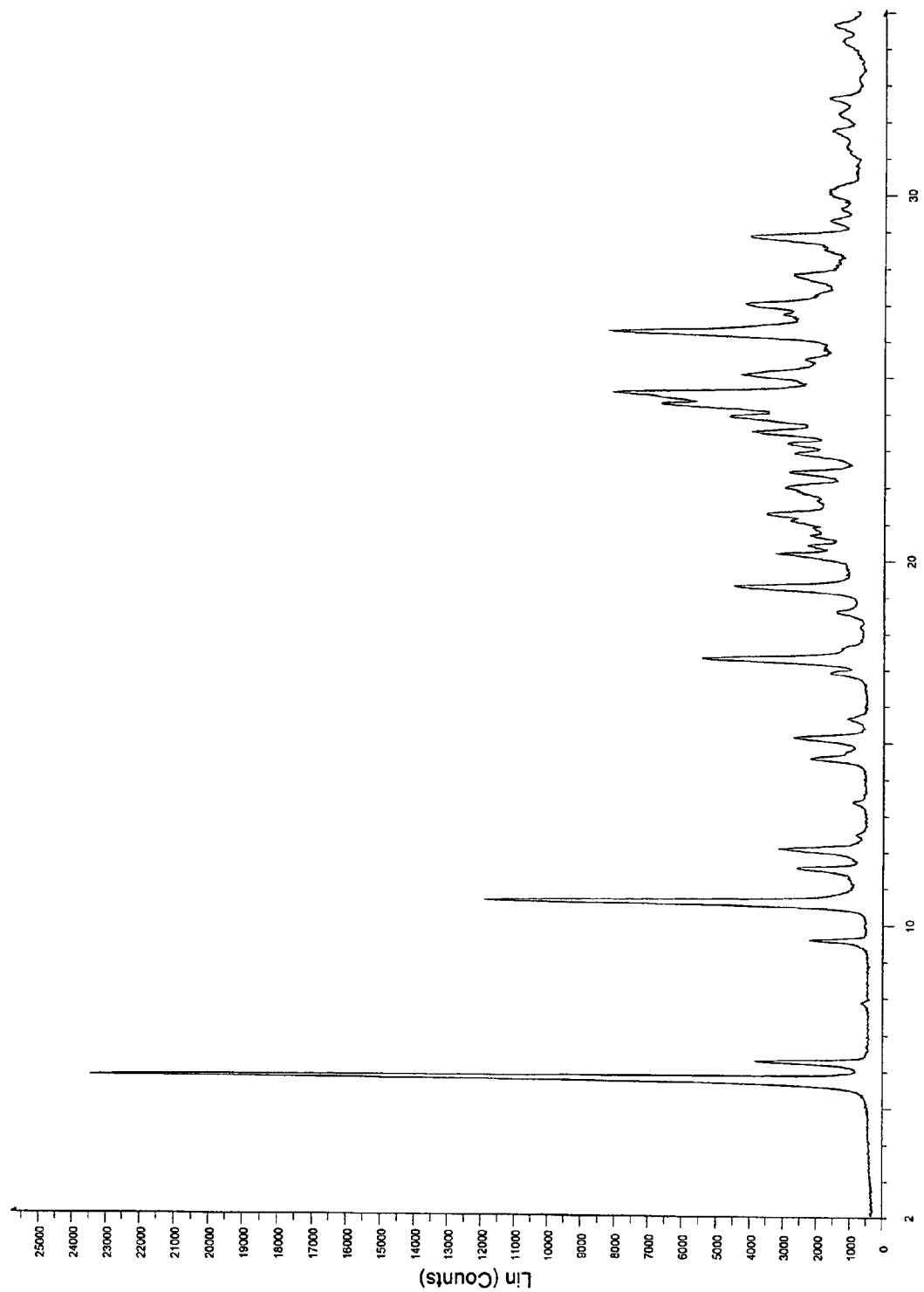
FIG. 4. XRPD spectra of erlotinib hydrochloride hemihydrate Form II.
Figure 6:
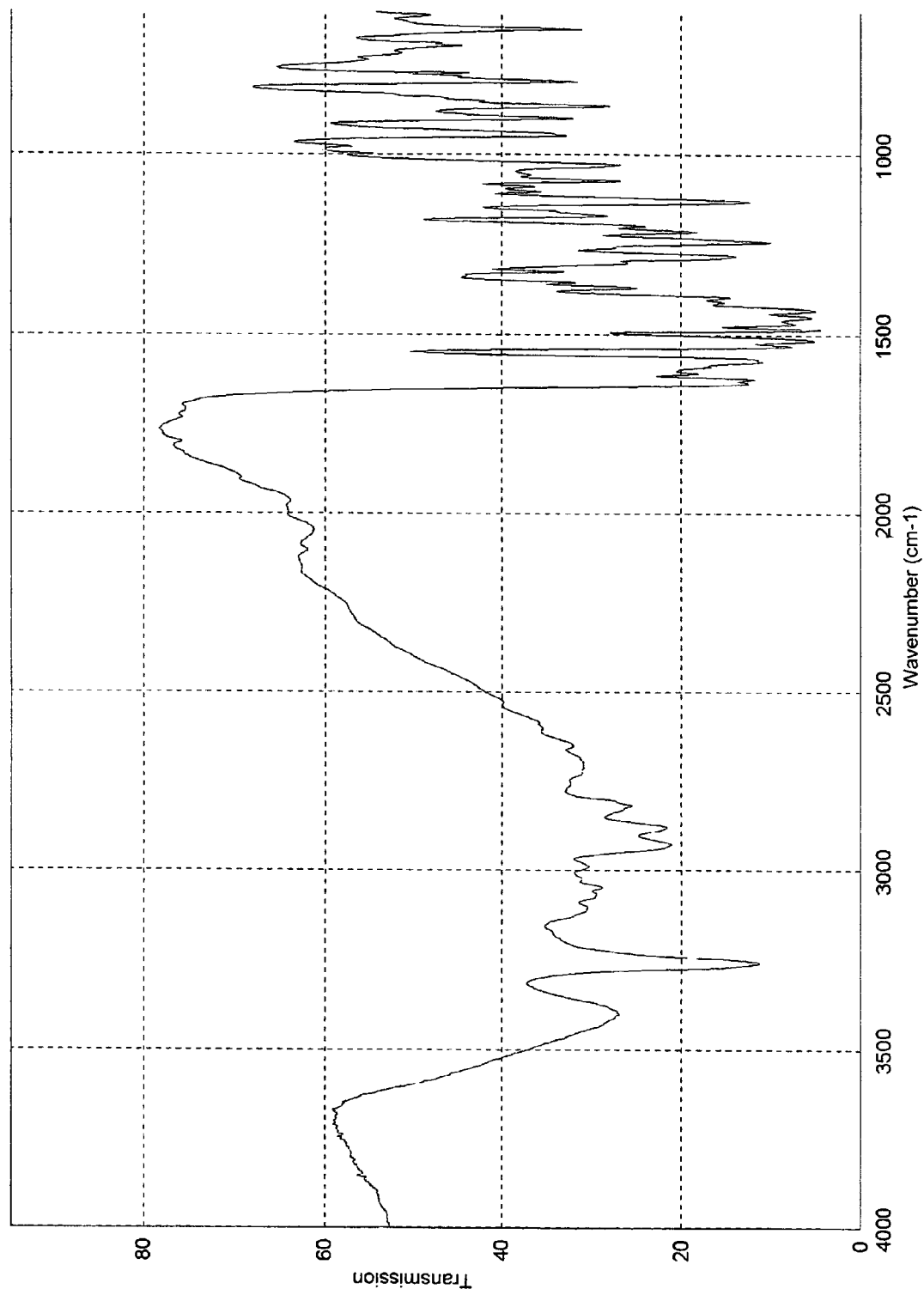
FIG. 6. FT-IR spectra of erlotinib hydrochloride hemihydrate Form II.

Two preferred hemihydrates are: erlotinib hydrochloride hemihydrate Form I which can be characterized by XRPD peaks at 2θ of 5.8, 9.4, 10.0, 11.1, 11.6, 17.5, 18.6, 24.9, and 26.8+/−0.2 degrees, or FT-IR peaks at 900, 950, 1152, 1216, 1484, 3254, 3327, and 3382+/−4 cm$^{-1}$, and erlotinib hydrochloride hemihydrate Form II which can be characterized by XRPD peaks at 2θ of 5.8, 10.6, 12.1, 14.6, 15.1, 17.3, 19.3, 24.3, and 26.3, +/−0.2 degrees or FT-IR peaks at 649, 867, 901, 948, 1029, 1073, 1213, 1242, 1355, 1431, 1484, 1624, and 3401+/−4 cm$^{-1}$. The crystalline hemihydrate Forms I and II can normally be identified by either the XRPD peaks or FT-IR peaks, and in practical terms will typically exhibit both. The peaks are not exhaustive. For example relatively pure Form I will generally exhibit the following XRPD peaks: 5.8, 6.3, 9.4, 10.0, 11.1, 11.6, 12.5, 13.4, 14.4, 14.8, 15.1, 16.4, 17.5, 18.1, 18.6, 20.1, 20.4, 20.7, 21.4, 22.1, 23.0, 23.3, 24.0, 24.3, 24.9, 25.3, 26.8, 27.9, 28.5, 28.8, 29.3, 29.8, 30.3, 33.1+/−0.2 degrees and/or the following FT-IR peaks: 628, 649, 685, 783, 852, 861, 887, 894, 900, 941, 950, 975, 1029, 1048, 1075, 1096, 1132, 1152, 1170, 1198, 1216, 1243, 1288, 1323, 1335, 1354, 1365, 1372, 1392, 1430, 1449, 1465, 1484, 1516, 1531, 1572, 1633, 1859, 2675, 2728, 2809, 2818, 2878, 2917, 2936, 3048, 3065, 3254, 3327, 3382+/−4 cm$^{-1}$. Indeed, Form I in relatively pure state (chemically and morphologically) will exhibit an XRPD pattern that substantially corresponds to FIG. 1 and an FT-IR that substantially corresponds to FIG. 3. Likewise, Form II will exhibit an XRPD and/or FT-IR that substantially corresponds to FIGS. 4 and 6, respectively.

The erlotinib hydrochloride hydrates of the present invention can be prepared by forming an aqueous solution of erlotinib hydrochloride in water, such as by dissolving the salt therein or forming it in situ, followed by crystallization of an erlotinib hydrochloride hydrate. The Form which may be obtained depends among others on the concentration of erlotinib hydrochloride in water, the crystallization temperature, the crystallization time and if stirring is applied during crystallization. Generally it is preferred that the aqueous solution does not contain an organic solvent, though minor ($\leqq$40%) or trace amounts ($\leqq$2%) can be present. The temperature is typically low, such as 20° C. or less and generally 10° C. or less. Stirring is usually avoided, at least on small scale. Seeding crystals may also be used during the precipitation.

For instance for making the pure hemihydrate Form I, a concentration of about 1% of erlotinib hydrochloride by weight in water can be used as the aqueous solution and crystallization can be performed at about 4° C. for 28 days without stirring.

For making the pure hemihydrate Form II, a lower concentration of about 0.6% of erlotinib hydrochloride by weight in water is used and crystallization is performed at about 4° C. for 4 days without stirring.

Pure Form I and pure Form II should be understood as substantially free of any other Forms of erlotinib hydrochloride hydrate or erlotinib hydrochloride.

It is observed that under the same circumstances as used to prepare hemihydrate Form I and Form II described above but with stirring during the crystallization period, a mixture of erlotinib hydrochloride Form B and the hemihydrate may be obtained.

Similar results may be obtained if an organic solvent is used as a co-solvent or anti-solvent. The obtained mixture may be a mixture of a hydrate with any other crystalline erlotinib hydrochloride Form, such as the prior art Forms A, B or E. It should be understood that such a mixture of compounds is contemplated as being within the scope of the invention as long as a crystalline hydrate compound is present, especially in amounts of 10% or greater.

The erlotinib hydrochloride hydrates may also be prepared by contacting erlotinib base with aqueous hydrochloric acid in an aqueous environment. Erlotinib free base may be dissolved in an aqueous hydrochloride solution to form the erlotinib hydrochloride solution in situ. The erlotinib hydrochloride hydrate may be crystallized from this solution as described above. Generally 1 to 1.5 equivalents of HCl is used.

The solubility of hydrated forms is usually less than the solubility of anhydrous forms. This reduced solubility may be used as an advantage for the purification of the compounds.

The hydrated Forms may lose their bonded water by heating, by placing the compound under vacuum, or by recrystallizing under removal of water with, for instance, a Dean Stark trap to form a non-hydrated erlotinib hydrochloride Form. Depending on the circumstances used, any of the prior art Forms (e.g., Form A, Form B, or Form E) may be obtained.

In some embodiments, it may be advantageous to purify erlotinib or the intended salt thereof via the hydrates of the present invention. Thus, the crystalline erlotinib hydrochloride hydrate of the present invention is formed as described above and converted to the desired erlotinib compound. For example, by using the hydrate as a starting material to recrystallize erlotinib hydrochloride as Form A, Form B, or Form E, different impurities may be removed by the two crystallizations being carried out under different solvent and crystallization conditions. Generally the recrystallization is carried out in a non-aqueous solvent system, i.e., consisting or comprising an organic solvent especially an alcoholic solvent or trifluorotoluene, although water can also be present as described above. Preferably the crystallization conditions as described in the prior art for the preparation of these specific Form A, Form B or Form E are used.

The invention also relates to the use of erlotinib hydrochloride hydrates and their pharmaceutical compositions as a medicament. Preferably the use is for the treatment of cancer wherein the cancer is from the group of brain, squamous cell, bladder, gastric, pancreatic, hepatic, glioblastoma multiform, head, neck, esophageal, prostate, colorectal, lung, renal, kidney, ovarian, gynecological, thyroid, non-small cell lung (NSCLC), refractory, ovarian, or head and neck cancer.

The pharmaceutical composition can be in the form of enteral, parenteral or transdermal administration. The composition can be administered orally in the form of tablets, capsules, solutions, suspensions or emulsions. The composition can also be administered in the form of an injection solution or suspension or infusion solution, or transdermally with for instance a patch. Pharmaceutical compositions can be obtained in a way which is common for a person skilled in the art.

The pharmaceutical compositions comprise a hydrate compound of the invention, or a mixture of compounds thereof, typically in a therapeutically effective amount, and a pharmaceutically acceptable excipient. Suitable dosage regimens comprise from 0.001 to 100 mg/kg/day.

Suitable excipients include solid inert diluents or fillers such as for example lactose, starches, calcium hydrogen phosphate etc., or liquids such as water, alcohols, paraffin's glycerol or polyols etc, and waxes etc. which will be apparent for the skilled persons in the art of preparing pharmaceutical compositions.

EXAMPLES

Figure 2:
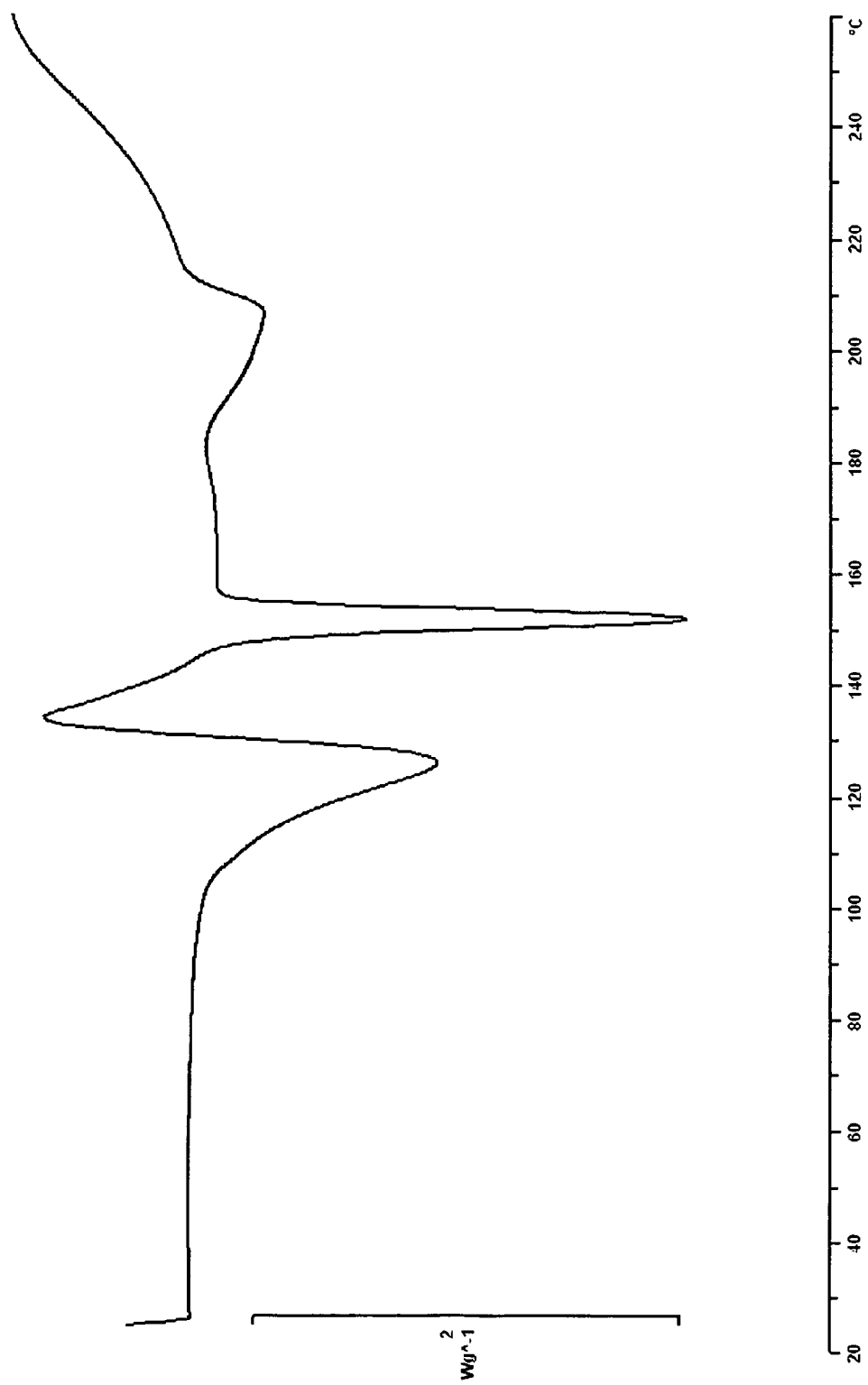
FIG. 2. DSC spectra of erlotinib hydrochloride hemihydrate Form I.

Hemihydrate Form I 0.5 g of anhydrous erlotinib hydrochloride was dissolved in 50 ml of demi-water at reflux. The hot solution was left unagitated at 4° C. for 28 days, during which slow crystallisation occurred. The solid was isolated by careful filtration over a P3-glass filter (reduced pressure) and air dried overnight at ambient conditions. Off-white to pale beige bunches of fibre-like crystals were obtained. The yield was 170 mg. (Analytical Data in FIGS. 1-3)

Figure 5:
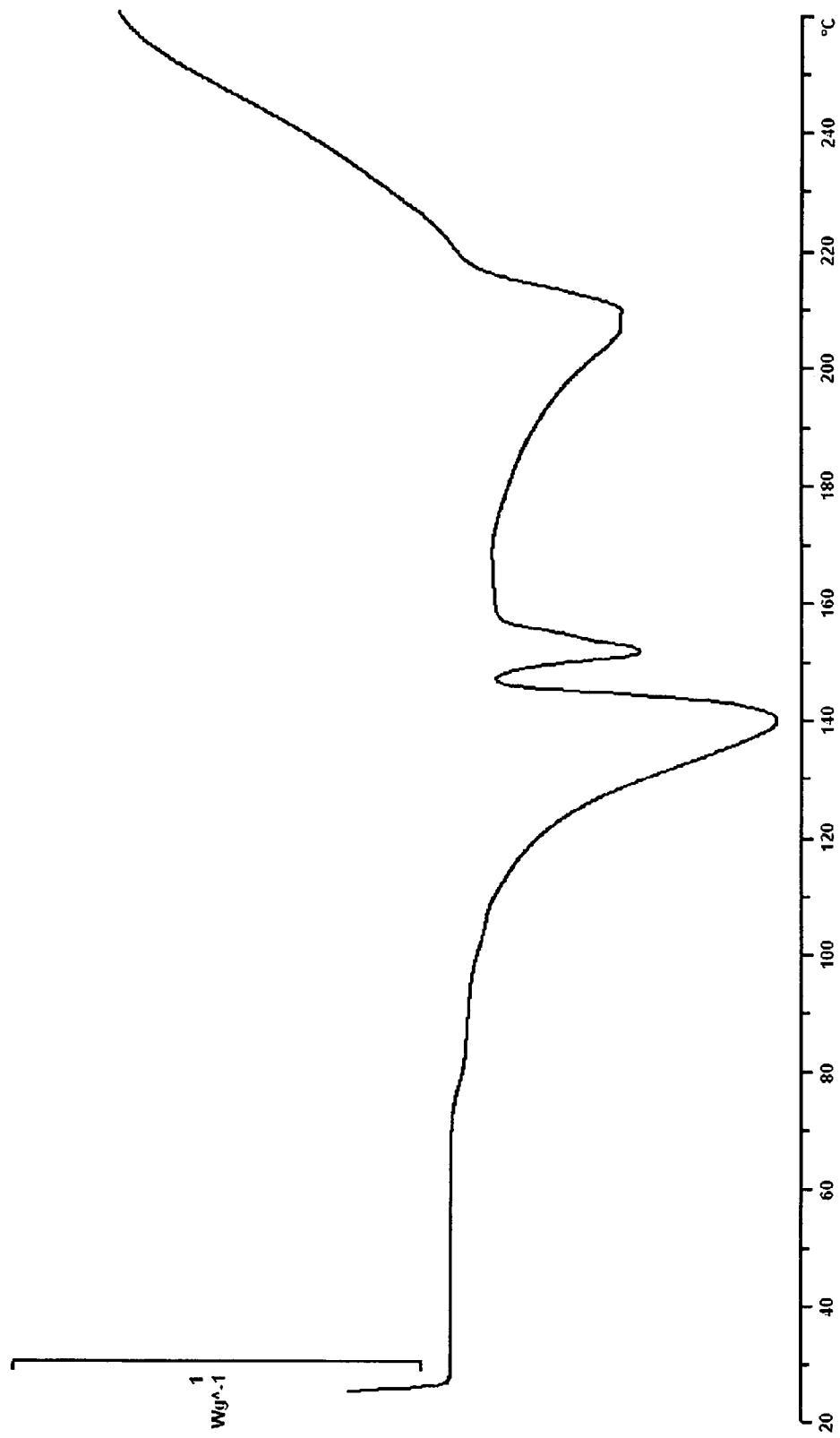
FIG. 5. DSC spectra of erlotinib hydrochloride hemihydrate Form II.

Hemihydrate Form II 0.3 g of anhydrous erlotinib hydrochloride was dissolved in 50 ml of demi-water at reflux. To the hot solution, a few mg of erlotinib hydrochloride hemihydrate Form I was added as seed. Subsequently, the solution was placed at 4° C. and left unagitated at 4° C. for 4 days, during which slow crystallisation occurred (crystals stuck at the wall of the flask). The crystals were scratched from the wall using a spatula, resulting in some additional nucleation. The suspension was left at 4° C. for an additional 2 hours. The solid was isolated by filtration over a P3-glass filter (reduced pressure, rapid) and air dried at R.T. and under ambient conditions for about 4 days. Pale yellow lumps of sticky powder were obtained. The yield was 300 mg.
(Analytical Data in FIGS. 4-6)

Each of the patents and patent applications mentioned above are incorporated herein by reference. The invention having been described it will be obvious that the same may be varied in many ways and all such modifications are contemplated as being within the scope of the invention as defined by the following claims.

I claim:

1. A crystalline erlotinib hydrochloride hydrate.
2. The hydrate according to claim 1, which is a crystalline erlotinib hydrochloride hemihydrate.
3. The hemihydrate according to claim 2, which is Form I characterized by XRPD peaks at 2θ of 5.8, 9.4, 10.0, 11.1, 11.6, 17.5, 18.6, 24.9, and 26.8 +/−0.2 degrees, or FT-IR peaks at 900, 950, 1152, 1216, 1484, 3254, 3327, and 3382+/−4 cm$^{-1}$.
4. A hemihydrate according to claim 3, wherein said crystalline erlotinib hydrochloride hemihydrate exhibits an XRPD that substantially corresponds to FIG. 1, and exhibits an FT-IR that substantially corresponds to FIG. 3.
5. A hydrate according to claim 2, which is Form II characterized by XRPD peaks at 2θ of 5.8, 10.6, 12.1, 14.6, 15.1, 17.3, 19.3, 24.3, and 26.3, +/−0.2 degrees, or FT-IR peaks at 649, 867, 901, 948, 1029, 1073, 1213, 1242, 1355, 1431, 1484, 1624, and 3401+/−4 cm$^{-1}$.
6. A hemihydrate according to claim 5, wherein said crystalline erlotinib hydrochloride hemihydrate exhibits an XRPD that substantially corresponds to FIG. 4, and exhibits an FT-IR that substantially corresponds to FIG. 6.
7. A pharmaceutical composition comprising a crystalline erlotinib hydrochloride hydrate according to claim 1, and at least one pharmaceutically acceptable excipient.
8. The pharmaceutical composition according to claim 7, wherein said crystalline erlotinib hydrochloride hydrate is crystalline erlotinib hydrochloride hemihydrate Form I or Form II.
9. A process for the preparation of a hydrate of erlotinib hydrochloride, which comprises crystallizing an erlotinib hydrochloride hydrate from an aqueous solution of erlotinib hydrochloride.
10. The process according to claim 9, wherein said crystallization is carried out at a temperature of 20° C. or less.
11. The process according to claim 10, wherein said crystallization is carried out without agitation.
12. The process according to claim 10, wherein said aqueous solution contains no more than trace amounts of an organic solvent.
13. The process according to claim 9, wherein said aqueous solution of erlotinib hydrochloride has a concentration of about 1% of by weight in water and said crystallizing is carried out at 4° C. without stirring; and said process produces crystalline erlotinib hydrochloride hemihydrate Form I.
14. The process according to claim 9, wherein said aqueous solution of erlotinib hydrochloride has a concentration of about 0.6% of by weight in water and said crystallization is carried out at about 4° C. without stirring; and said process produces crystalline erlotinib hydrochloride hemihydrate Form II.
15. A process for making crystalline erlotinib anhydrate, which comprises crystallizing an erlotinib hydrochloride hydrate from an aqueous solution of erlotinib hydrochloride; and
recrystallizing said erlotinib hydrochloride hydrate from a non-aqueous solvent system to form an anhydrous erlotinib hydrochloride of Form A, Form B, or Form E.
16. The process according to claim 15, wherein said non-aqueous solvent system is a mixture of 2B-ethanol and water and said anhydrous erlotinib hydrochloride is Form B.
17. The process according to claim 15, wherein said non-aqueous solvent system is trifluorotoluene and said anhydrous erlotinib hydrochloride is Form E.

* * * * *